United States Patent [19]
Cochrum et al.

[11] Patent Number: 5,773,033
[45] Date of Patent: *Jun. 30, 1998

[54] FIBRINOGEN/CHITOSAN HEMOSTATIC AGENTS

[75] Inventors: Kent C. Cochrum; Harold R. Parker; Maggie M. C. Chiu, all of Davis, Calif.

[73] Assignee: The Regents of the University of California, Oakland, Calif.

[*] Notice: The term of this patent shall not extend beyond the expiration date of Pat. No. 5,510,102.

[21] Appl. No.: 636,247

[22] Filed: Apr. 23, 1996

Related U.S. Application Data

[63] Continuation-in-part of Ser. No. 377,775, Jan. 23, 1995, Pat. No. 5,510,102.

[51] Int. Cl.$^6$ .................................................... A61L 25/00
[52] U.S. Cl. ........................... 424/530; 606/215; 424/532
[58] Field of Search ................................ 424/78.08, 530, 424/532

[56] References Cited

U.S. PATENT DOCUMENTS

| | | | |
|---|---|---|---|
| 4,394,373 | 7/1983 | Malette et al. | 514/55 |
| 4,427,650 | 1/1984 | Stroetmann | 424/45 |
| 4,744,933 | 5/1988 | Rha et al. | 264/4.3 |
| 4,749,620 | 6/1988 | Rha et al. | 428/402.2 |
| 4,853,220 | 8/1989 | Clemmensen et al. | 514/21 |
| 5,226,877 | 7/1993 | Epstein | 604/35 |
| 5,292,362 | 3/1994 | Bass et al. | 106/124 |
| 5,510,102 | 4/1996 | Cochrum | 424/78.08 |

OTHER PUBLICATIONS

Karl H. Siedentop et al, Autologous Fibrin Tissue Adhesive, Laryngoscope 95: 1074–1076, Sep. 1985.

David M. Harris et al, Autologous Fibrin Tissue Adhesive Biodegradation and Systemic Effects, Laryngoscope 97: 1141–1144, Oct. 1987.

L. H. Durham et al, A Method for Preparation of Fibrin Glue, The Journal of Laryngology and Otology, vol. 101, pp. 1182–1186, Nov. 1987.

Nicolas E. Stathakis et al, Cryoprecipitation of Fibrin–Fibrinogen Complexes Induced by the Cold–insoluble Globulin of Plasma, Blood, vol. 51, pp. 1211–1222, No. 6 (Jun.), 1978.

*Primary Examiner*—Peter F. Kulkosky
*Attorney, Agent, or Firm*—Hana Verny

[57] ABSTRACT

Autologous fibrinogen and chitosan containing hemostatic adhesive agents having strong hemostatic properties when applied to a bleeding wound or vessel. Fibrinogen is isolated and purified using ammonium sulphate precipitation in slow incremental portions.

15 Claims, 2 Drawing Sheets

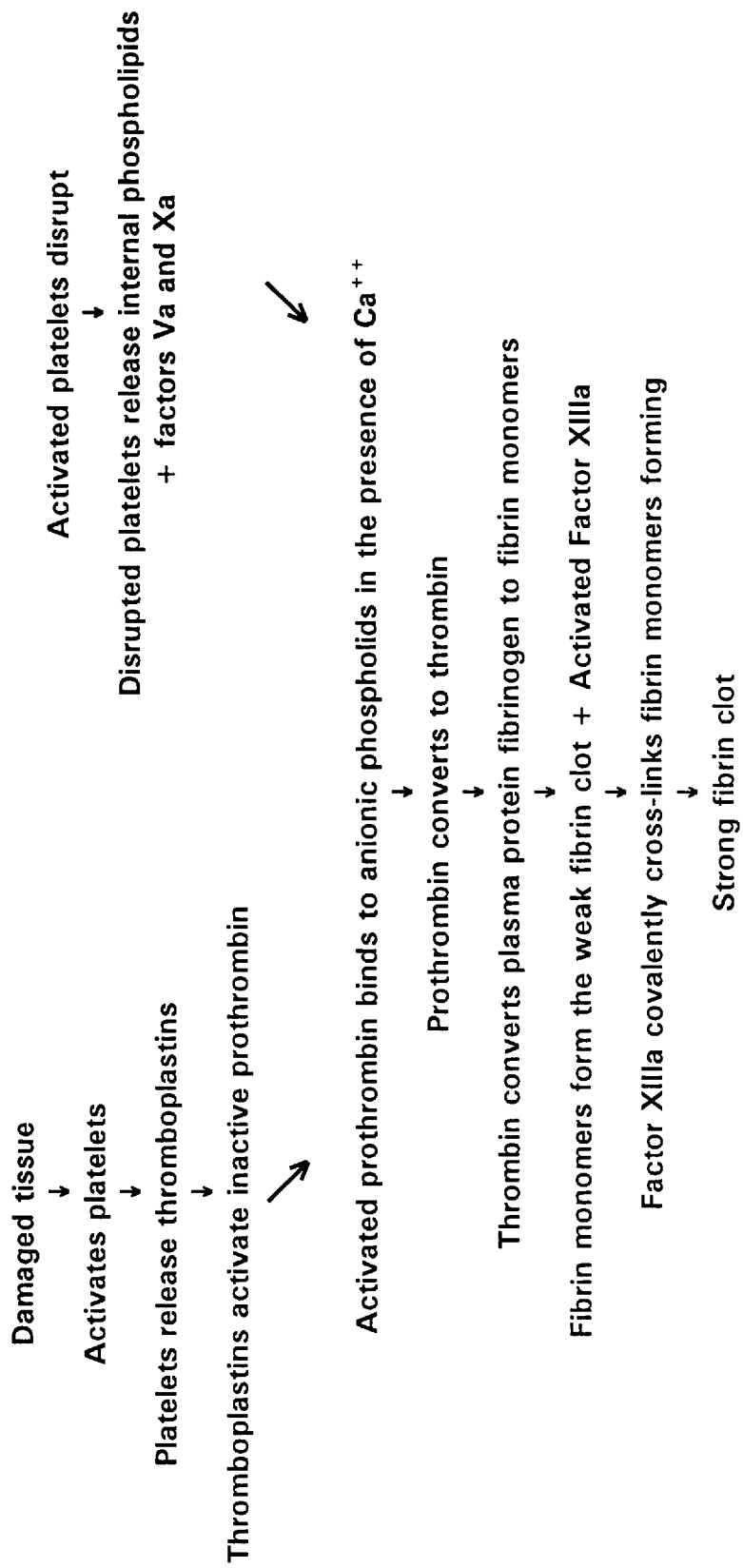

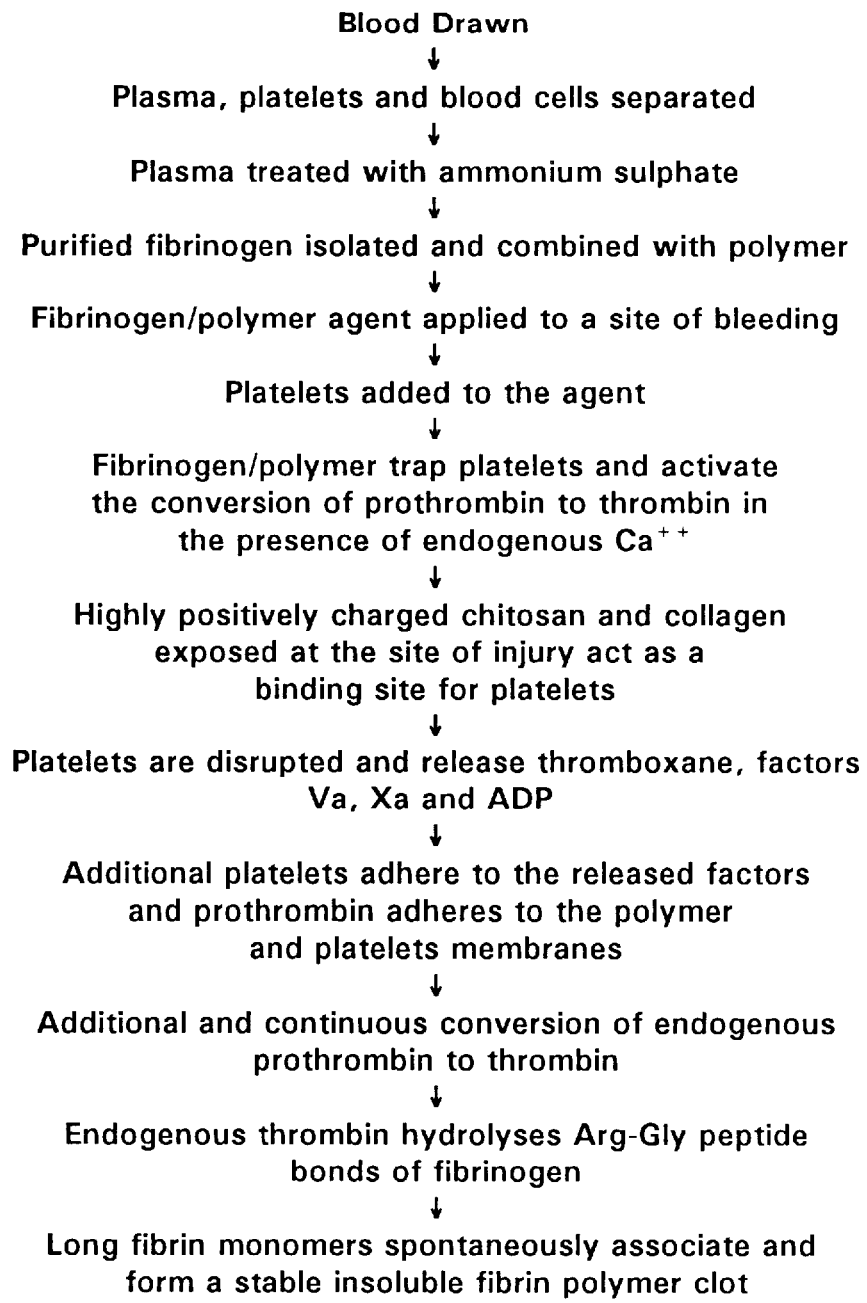

ic of 5,773,033

FIBRINOGEN/CHITOSAN HEMOSTATIC AGENTS

This is a continuation-in-part application of Ser. No. 08/377,775, filed Jan. 23, 1995, issued as U.S. Pat. No. 5,510,102 on Apr. 23, 1996.

BACKGROUND OF THE INVENTION

Field of Invention

This invention concerns hemostatic adhesive agents comprising autologous isolated and purified fibrinogen in combination with a biocompatible polymer. In particular, this invention concerns the fibrinogen and polymer containing hemostatic agents containing fibrinogen isolated from autologous plasma and purified of other plasma proteins, and a biocompatible chitosan. The agent has strong hemostatic properties when applied to a bleeding wound or vessel where it facilitates a rapid formation of a polymer clot by activation of a patient's platelets and conversion of prothrombin to thrombin. The polymer component of the agent triggers and enhances the normal clotting mechanism.

BACKGROUND ART AND RELATED ART DISCLOSURES

Surgical biological glues have recently been used in a variety of surgical procedures. Among those most known and used are a fibrin glue or a gelatin-resorcin-formalin glue.

Fibrin glue is based on the basic physiological fibrinogen and thrombin functions. In the presence of calcium ions, activation of fibrinogen and fibrin-stabilizing factor XIII with thrombin produces a stable fibrin clot. Fibrin itself adheres to collagen, and factor XIII stimulates increased collagen biosynthesis by activating fibroblasts. The application of fibrin glue in wound healing allows restoration of the structural properties of the wound by the glue and stimulation of repair by the components that comprise the glue. Fibronectin and cold insoluble globulin also enhance fibroblast proliferation.

Current methods of preparing fibrin glue have improved recovery of a variety of coagulation proteins including clotting factors and thrombin.

While hemostatic action of fibrin glue has been described and shown to act as a hemostatic agent in hepatic and splenic trauma *J. Ped. Surg.,* 24:867 (1989); as a sealant of the common bile duct *Surgery,* 101:357 (1987); as a glue sealing pancreatic injuries *Am. J. Surg.,* 161:479 (1991), resections and anastomosis *Brit. J. Plast. Surg.,* 42:54 (1989); as a glue for microvascular anastomosis, and as a glue for treating aortic dissections *Ann. Thorac. Surg.,* 50:143 (1990), its toxicity and possible anaphylactic reactions are of great concern. Fatal reaction to the use of fibrin glue in deep hepatic wounds is described in *J. Trauma,* 31:408 (1991). This fatal reaction is believed to have been caused by activation and conversion of fibrinogen into a fibrin using a bovine thrombin resulting in anaphylactic shock leading to death.

The most common method of preparation of fibrin glue is by the simultaneous mixing of concentrated fibrinogen complex obtained from pooled human blood, bovine thrombin and ionic calcium immediately before use. The addition of the nonhuman, typically bovine, thrombin in the fibrin glue preparations used for treatment in humans, has resulted in severe and even fatal anaphylactic reactions, such as described above. Hemostasis abnormalities caused by antibodies to bovine proteins, such as bovine thrombin, which cross-react with human proteins including thrombin and factor V, have been reported in *J. Thorac. Cardiovac. Surg.,* 105:892 (1993). Similarly, foreign body reactions following the use of these fibrin bovine thrombin containing glues have been detected and described in *Eur. J. Pediatr. Surg.,* 2:285 (1992).

Another major problem connected with the currently used fibrin glues is due to the use of pooled human blood which may result in transmission of infectious diseases to a patient treated with the fibrin glue obtained from human donors, as described in *Opth. Surg.,* 23:640 (1992).

Additionally, while fibrin glues set very rapidly, in from three to five seconds, there is no increase in their adhesive strength after five minutes (*J. Biomed. Mater. Res.,* 26:481 (1992)).

Attempts to utilize autologous fibrin as tissue adhesive were described, for example, in *Laryngoscope,* 95:1074 (1985) where different methods of making fibrin tissue adhesive from a patient's own blood are evaluated. The described fibrin adhesive comprises a highly concentrated fibrinogen obtained by cryo-precipitation or by precipitation of fibrinogen with ethanol, centrifugation, or ammonium sulfate using saturated solution of purified ammonium sulfate. The precipitated fibrinogen is then combined with bovine thrombin and calcium chloride.

*Laryngoscope,* 97:1141 (1987) describes degradation studies of autologous fibrin tissue adhesive by the fibrinolysis inhibitor Σ-amino caprotic acid. The adhesive utilizes fibrinogen precipitated with ammonium sulfate as one component and bovine thrombin as the second component.

A method for preparation of fibrin glue for otorhinolaryngological operations is described in *J. Laryngology and Otology,* 101:1182 (1987). The glue consists of fibrinogen, factor XIII and aprotin (a bovine-derived fibrinolysis antifibrinolytic inhibitor) in combination with bovine thrombin and calcium chloride. Fibrinogen is precipitated with saturated solution of ammonium sulphate.

While these method seem to provide fibrin glues which fulfill the hemostatic function, they all require the presence of bovine thrombin, thereby introducing a foreign element which can cause immune reactions as well as disease transmission as described above.

It would be, therefore, advantageous to develop a new type of a biological hemostatic adhesive which would eliminate or reduce the use of bovine thrombin, or thrombin obtained from human donors, which can lead to a formation of antibodies to such bovine or human proteins, or which adhesive would avoid pooling of human blood which may result in transmission of infectious diseases. The new type of the hemostatic adhesive would avoid problems associated with the currently available fibrin glues.

It is, therefore, a primary object of this invention to provide hemostatic adhesive agents for surgical and other medical purposes which agents would be prepared from autologous blood and would eliminate or strongly reduce the risk of disease transmission or immunoreactions caused by introduction of foreign thrombin. The hemostatic adhesive agents would be prepared from the isolated and purified fibrinogen obtained from the patient's own blood, combined with biocompatible polymers and would avoid the use of foreign proteins such as thrombin. The new agents would eliminate or strongly reduce the risk of immunogenic reactions, would significantly promote healing of tissues and would be, additionally, less expensive than currently available glues.

The autologous purified isolated fibrinogen in combination with a biocompatible polymer useful as an hemostatic surgical adhesive agent has not been previously reported or disclosed.

All patents, patent applications and references cited herein are hereby incorporated by reference.

SUMMARY

One aspect of the invention is a hemostatic adhesive agent comprising a purified isolated fibrinogen in combination with a biocompatible polymer.

Another aspect of the invention is a hemostatic adhesive agent comprising an autologous purified isolated fibrinogen in combination with a biocompatible chitosan.

Another aspect of the invention is a method for isolation of fibrinogen from other plasma protein by using slow precipitation with ammonium sulphate added in small increments for extended periods of time.

Another aspect of the invention is a hemostatic adhesive agent comprising a purified isolated fibrinogen in combination with a cationic or anionic chitosan.

Another aspect of the invention is a method for use of the hemostatic adhesive agent comprising administering to a site of injury or bleeding an admixture of purified isolated fibrinogen and chitosan.

Another aspect of the invention is a method for use of the hemostatic adhesive agent, comprising administering separately to a site of injury or bleeding a purified isolated fibrinogen and chitosan.

Another aspect of this invention is a process for isolation and purification of fibrinogen, comprising steps:

(a) obtaining plasma from whole blood;

(b) treating the plasma with an ammonium sulphate solution in such a way that the concentration of ammonium sulphate in plasma does not exceed 25%;

(c) separating the fibrinogen from the plasma by centrifugation; and (d) detecting the presence or absence of other plasma proteins.

An additional aspect of this invention is a process for preparation of purified isolated fibrinogen wherein ammonium sulphate is dissolved in an aqueous solvent in the amount of 65–73 g/100 ml, and is added in increments of about 0.50–0.62 ml/minute for about 15–20 minutes.

BRIEF DESCRIPTION OF FIGURES

FIG. 1 is a scheme illustrating the physiological process of coagulation.

FIG. 2 is a scheme illustrating the hemostatic process using a fibrinogen/polymer hemostatic adhesive agent.

DEFINITIONS

As used herein:

"Hemostatic adhesive agent" also called "fibrinogen polymer" means a solution or other preparation which contains essentially two components: a purified isolated fibrinogen and a physiologically acceptable biocompatible and FDA-approved chitosan.

"Cascade-like effect" means a sequence of reactions beginning with applying the hemostatic agent of the invention to the wound or incision, where the fibrinogen initiates conversion of prothrombin to thrombin and the polymer contained in the hemostatic agent enhances a formation of a polymer clot by trapping endogenous or exogenous platelets. This clot rapidly triggers release of factors Va, Xa and thromboplastins from the platelets added to the fibrinogen component of the hemostatic agent. The release of thromboplastins from the platelets initiates the physiological clotting process.

"Exogenous platelets" are platelets, autologous or not, added to the fibrinogen component.

"Endogenous platelets" are platelets present in the circulating blood of the patient.

DETAILED DESCRIPTION OF THE INVENTION

The current invention concerns a novel type of hemostatic adhesive agents comprised of isolated and purified fibrinogen and a biocompatible chitosan polymer.

The hemostatic adhesive agents are prepared from, and contain, a purified fibrinogen isolated from plasma, using a novel process for fibrinogen isolation and purification, combined with a physiologically acceptable biocompatible polymer. The combination of the purified isolated fibrinogen with the polymer forms, in the presence of endogenous or exogenous added platelets, an adhesive which has very strong adhesive properties and a very rapid onset of hemostatic action. Adhesivity strength and the speed with which the hemostatic action sets depend on the fibrinogen concentration and on the type and amount of the chitosan polymer.

In essence, the invention utilizes certain aspects of the natural physiological process of blood coagulation, such as activation of platelets, release of thromboplastins and other coagulation factors and cofactors, conversion of prothrombin to thrombin, conversion of fibrinogen to fibrin monomers and formation of a fibrin clot. These aspects of the natural coagulation process are enhanced by adding the biocompatible chitosan polymer.

One of the two primary components of the hemostatic adhesive agent is fibrinogen. The second component is the chitosan polymer. To obtain fibrinogen having superior coagulating properties, the fibrinogen is isolated and purified in such a way that the presence of other proteins, such as euglobulins, pseudoglobulins and albumin, is eliminated. Isolation of fibrinogen from other proteins greatly enhances its response to endogenous thrombin, by forming long fibrin monomers which spontaneously associate and form a stable insoluble fibrin polymer clot, when the fibrinogen is applied in combination with chitosan and in presence of platelets added separately, to a site of bleeding or injury. This fibrin polymer clot initiates a hemostatic process which then continues in a cascade-like fashion.

Cascade-like hemostasis is achieved by rapid and continuous trapping, activation and disruption of the platelets initially added to the fibrinogen and polymer agent followed by trapping, activation and disruption of platelets present in the patient's own blood. The disruption of the platelets leads to a release of coagulating factors from the platelets and to a fast conversion of prothrombin to thrombin. Due to this cascade-like effect, the hemostatic clot forms quicker and the adhesive strength of the hemostatic clot increases more rapidly than during normal physiological coagulation, where the coagulation time is about 3–5 minutes and during which the maximal adhesive strength of the clot is obtained physiologically or from other known fibrin glues. Moreover, as the polymer is not subject to a physiological regulation by lysis, the cascade effect continues until complete hemostasis occurs.

The current invention provides several advantages over the fibrin glues known previously.

One of the advantages of the invention is that the fibrinogen is prepared from the patient's own blood, thereby eliminating possible immunogenic reactions as well as the possibility of transmission of infectious diseases, toxins or parasites. Another advantage is that by using the hemostatic adhesive of the invention, the use of exogenous (typically bovine) thrombin is eliminated. The agent of the invention activates endogenous platelets, and promotes and enhances conversion of endogenous prothrombin to thrombin in an amount sufficient to convert the fibrinogen to fibrin clot, eliminating the need for exogenous thrombin. The presence of thrombin in all other known fibrin glues is necessary. The absence of need to use exogenous thrombin prevents transmission of infectious diseases such as HIV and hepatitis, or parasites.

Other advantages of the current hemostatic agent are the instant hemostasis, adherence of damaged tissue together, and promotion of the healing process by combination of purified fibrinogen with the patient's own thrombocytes.

I. Normal Physiological Mechanism of Blood Coagulation

The physiological mechanism of blood coagulation and clotting is based on properties of plasma proteins and platelets. These two blood components contain all the factors required for clotting.

Processes involved in normal physiological blood clotting are seen in FIG. 1.

Two major plasma proteins involved in blood clotting are fibrinogen and prothrombin. The essential reaction in coagulation of the blood is the enzymatic conversion of the soluble protein fibrinogen into the insoluble protein fibrin by thrombin. Fibrinogen exists in the circulating blood as such and can be precipitated from plasma. Thrombin is formed from an inactive circulating precursor, prothrombin, during tissue injury, bleeding or blood loss. The activation of prothrombin depends on the presence of calcium ions ($Ca^{++}$) and thromboplastins which are released or derived from damaged tissues, disintegrating platelets or plasma itself. This process, or certain aspects of it are advantageously utilized in the current invention.

Normally, when the tissue is injured and bleeding occurs, it responds physiologically by activation of platelets followed by a release of thromboplastins. Thromboplastin (plasma factor III) is a substance that assists in the clotting of blood by initiating the conversion of the inactive prothrombin (plasma factor II) to the active thrombin. Such conversion occurs in the presence of calcium ions (plasma factor IV).

Thrombin is a very potent serine protease that causes clotting by converting fibrinogen (plasma factor I) to fibrin. Thrombin is so potent that it can coagulate at least 600 times its weight of fibrinogen. The velocity of the thrombin-fibrinogen reaction is further accelerated by increased concentration of thrombin. Thrombin, which can act in the absence of $Ca^{++}$, enzymatically splits off a highly acidic fibrinopeptide from the fibrinogen by hydrolysing arginine-glycin peptide bonds in the fibrinogen, thereby generating fibrin monomers. The remainder of the fibrinogen then polymerizes to form fibrin.

Fibrin is an elastic, thread-like insoluble protein monomer which forms the network of the hemostatic clot. The insoluble fibrin monomers spontaneously associate in a regularly staggered array to form the insoluble fibrin polymer clot. The initial fibrin clot formed within first 3–5 seconds of bleeding is a rather weak structure, held together only by a noncovalent array of the fibrin monomers.

Additionally, thrombin converts fibrin stabilizing factor XIII, to active factor XIIIa. Factor XIIIa is an enzyme transglutaminase which covalently cross-links fibrin monomers by forming specific isopeptide bonds thereby strengthening the fibrin clot. The freshly formed threads are extremely adhesive, sticking to each other, to the blood cells, to the tissues, and to certain foreign surfaces. This adhesiveness makes the clot an effective hemostatic agent. All these enzymatic reactions, of course, take certain time, typically between 3–5 minutes, within which the final hemostatic clot forms. The time of clot formation also depends on the extent of the bleeding.

Aside from fibrinogen, prothrombin, thromboplastin, and calcium (plasma factors I and IV), there are other plasma factors involved in normal physiological coagulation reactions. These factors are plasma factors proaccelerin (V), proconvertin (VII), antihemophilic globulin (VIII), Christmas factor (IX), Stuart-Prower factor (X), plasma thromboplastin antecedent (XI), Hageman factor (XII) and fibrin stabilizing factor (XIII). Plasma factor V (proaccelerin) acts, when activated to factor Va, as a cofactor for the activated enzyme factor Xa that activates prothrombin. These and all other above named factors are involved in the normal blood coagulation processes. Some of them are also involved in the hemostatic action of the current hemostatic agent as seen in FIG. 2.

Calcium ions are essential for clotting. They are necessary for the formation of active thromboplastin and for the conversion of prothrombin to thrombin in the first phase of the coagulation process. They are not necessary and do not influence the action of thrombin on fibrinogen in the second phase of the coagulation. Consequently, the current invention does not require additional calcium ions.

The activation of prothrombin occurs on the platelets and requires platelet anionic phospholipids, activated factor Va, activated factor Xa and calcium ions. The platelet anionic phospholipids, which are normally situated on the internal side of the platelet plasma membrane, are exposed as a result of the platelet disruption. These phospholipids bind $Ca^{++}$ and prothrombin. Prothrombin activates factor V, normally present in the platelets which is activated by Va factor. The activated Va factor binds to the specific receptor on the platelet membrane and by itself the Va factor acts as a receptor for factor Xa. Factor Xa binds to the prothrombin and being a serine protease, cleaves the inactive amino portion of the prothrombin, thereby activating prothrombin to thrombin. This step is advantageously utilized when the platelets are trapped within the fibrinogen/polymer hemostatic agent according to the invention.

The above-discussed coagulation properties of fibrinogen are widely utilized for fibrin glues. These glues are typically prepared from fibrinogen obtained from bovine or pooled human blood in combination with bovine or human thrombin. These foreign proteins may lead to the development of recipients' immunoreactions in case of use of fibrinogen or thrombin of different species, or to transmission of infections between individuals caused by the use of fibrinogen and/or thrombin of the same species but of different individuals.

Previously known surgical fibrin glues made up of pooled human fibrinogen activated by bovine thrombin are used extensively in Europe and attempts have been made to introduce these glues in the United States. The FDA, however, has been reluctant to approve these fibrin glues because of the risk of transmission of animal and human viruses and other infections and because of the immunological reactions caused by bovine thrombin. The current invention overcomes these problems and provides many additional advantages, as enumerated above.

For the above reasons, attempts were previously made to prepare autologous fibrin tissue adhesives. Resulting autologous fibrin tissue adhesives decreased to a certain degree the risk of transfer of viral and other infections and possible immune reactions. However, as in all of them the second component, thrombin, is needed and as this thrombin is of exogenous, most often bovine, origin, the risk of immunoreactions or transmission of infectious and parasitic diseases is not eliminated because thrombin itself may be contaminated.

II. Hemostatic Adhesive Agents of the Invention

Hemostatic adhesive agents of the invention and their hemostatic actions differ from the prior fibrin glues in that they are completely autologous, and all their components are of autologous origin and are either present endogenously in sufficient amount to achieve hemostasis according to the invention or are added exogenously after being first isolated from the autologous blood. Therefore, the invention does not require addition of foreign cells, such as platelets, foreign proteins, such as thrombin, or other components, such as calcium ions.

The hemostatic agent according to the invention is typically prepared from purified and isolated fibrinogen, in combination with a physiologically acceptable and biocompatible chitosan polymer. The hemostatic adhesive agent consists of fibrinogen which is isolated from plasma and purified to remove other plasma proteins.

The hemostatic agent additionally contains a physiologically acceptable biocompatible polymer which is highly positively charged. The preferred polymer is chitosan added in ratio from about 0.1–10% of the polymer to about 90–99.9% of fibrinogen. The polymer causes rapid activation and aggregation of platelets, exogenous or endogenous, and thereby induces and increases hemostatic adhesive action of the hemostatic agent of the invention in a cascade-like manner.

The polymer is either a component of the hemostatic adhesive agent administered in admixture with fibrinogen or the polymer can be used separately from fibrinogen and administered to the site of injury either before or after fibrinogen is added, as the hemostatic adhesive agent.

Hemostatic agents of the invention therefore consist essentially of fibrinogen and a biocompatible chitosan polymer, preferably cationic chitosan.

For initiation of its hemostatic action, the agent additionally utilizes either exogenous or endogenous, preferably autologous, platelets. The combination of fibrinogen and platelets promotes clotting, adhesion and healing as described below.

In its most preferred form, the hemostatic adhesive agent is autologous, that is, it is prepared from the patient's own blood combined with the pure physiologically acceptable and biocompatible chitosans approved by the Food and Drug Administration for use in humans.

Autologous fibrinogen is prepared from patient's own blood which is separated into plasma, platelets and blood cells. The plasma is further processed as described below to yield purified fibrinogen isolated from other plasma proteins. The platelets which are also separated from the whole blood are preserved and combined with purified fibrinogen and the polymer immediately before administration to initiate a clotting process or they are added separately to the site of bleeding after the hemostatic agent is administered. The hemostatic agent of the invention is preferably prepared in the operating room at the time of surgery or treatment.

The method for achieving hemostasis according to the invention using hemostatic adhesive agents of the invention, is illustrated in FIG. 2.

The hemostatic plasma/polymer agent has a high ratio of fibrinogen to the polymer. Generally, the agent is composed of about 90% to about 99.9% of isolated and purified fibrinogen and from about 0.1% to about 10% of the polymer. When mixed and applied to a wound's bleeding surface or bleeding vessel, the polymer component when in combination with fibrinogen, triggers the normal clotting mechanism upon contact with the bleeding wound and aggregates and activates the exogenous and/or endogenous platelets. Activated platelets release thromboplastin and promote conversion of prothrombin to thrombin in the presence of endogenous $Ca^{++}$. While typically not necessary, calcium solution may be added, if for any reason the endogenous calcium would not be present in a sufficient amount. Highly positively charged chitosan, in combination with the fibrinogen, forms an array of fibers trapping and disrupting the platelets, and collagen exposed at the site of injury acts as an attractant binding site for the platelets. By forming the initial hemostatic clot, combined with additional binding sites for the platelets due to exposed collagen, more and more of the platelets and platelet debris is caught in this initial hemostatic clot.

The platelet activation, resulting from their contact with the hemostatic agent, followed by their disruption, leads to a release of factors Va and Xa and ADP, and initiation of conversion of prothrombin to thrombin. Meanwhile, additional platelets adhere to the factors released from the disrupted platelets, and prothrombin adheres to the chitosan polymer and to the platelets' membranes. As more and more endogenous platelets are activated in a cascade-like fashion, the original polymer clot is enlarged and, as it forms a clot matrix, it is also strengthened.

Such clot matrix is, under normal physiological conditions, formed only after the chain of reactions happens, as seen in FIG. 1, including the activation of platelets leading to the activation of prothrombin to thrombin, the activation of fibrinogen by thrombin, the conversion of fibrinogen to initial fibrin monomers, the formation of the weak fibrin clot and the strengthening of fibrin by cross-linking with factor XIIIa. The clot formed in response to the platelet activation then converts soluble fibrinogen to a stable fibrin clot. Such conversion occurs in the presence of factor XIIIa, a fibrin stabilizing factor, that catalyzes formation of peptide bonds between fibrin molecules, and in this way stabilizes the clot.

To the contrary, in the current invention, the clot matrix is formed quickly following the application of the hemostatic agent of the invention which delivers purified and isolated fibrinogen in combination with chitosan and separated platelets able to release coagulation factors, thereby instantly triggering the coagulation process at the site of the injury or bleeding, as illustrated in FIG. 2.

As seen in FIG. 2, the hemostasis according to the invention, as compared to the normal physiological coagulation process shown in FIG. 1, is much faster. Strength of the hemostatic polymer clot can be further increased by higher concentration of fibrinogen, by increased production of thrombin, or by addition of platelets during the entire time the adhesive is being applied. In the normal physiological coagulation process, after 3–5 minutes the strength of the normal clot does not increase. The new hemostatic agent forms a clot within five seconds and the process proceeds in controlled manner until complete hemostasis is achieved. Adhesivity of the agent is also controlled by the higher or lower concentration of the added polymer. When the concentration of the polymer is from 0.1–2%, the tensile strength of the fibrin monomers is lesser. When the polymer concentration is between 2–10%, the tensile strength of the fibrin monomers of the hemostatic clot is greater and the coagulation proceeds faster.

Using the current invention, isolated and purified fibrinogen and platelets are prepared from plasma as described below and in the Examples. A chosen polymer, preferably positively charged chitosan, is then added to the fibrinogen. Thus made adhesive is applied to the site of injury, such as the wound, venous incision, cut or rupture, or to the damaged tissue. The polymer acts rapidly as an extraneous impulse trapping and activating exogenously supplied or endogenously present platelets. Upon applying the fibrinogen-polymer agent to the site of injury, platelets activate conversion of prothrombin to thrombin in the presence of Ca++ and the physiological clotting begins rapidly and on a large scale, having readily available all the necessary clotting factors in high concentrations.

Highly positively charged chitosan and collagen exposed at the site of injury act as a binding site for platelets, which are disrupted and release thromboxane and coagulation factors Va, Xa and ADP. Additionally, endogenous platelets adhere to the released factors and prothrombin adheres to the polymer and to platelets' membranes, further promoting conversion of prothrombin to thrombin. Endogenously formed thrombin hydrolyses the fibrinogen arginine-glycine peptide bonds resulting in formation of long fibrin monomers. These monomers spontaneously associate and form a stable insoluble fibrin polymer clot.

The polymer which forms the initial clot becomes substantially strengthened by the platelets and platelets debris and its adhesivity is further enhanced by the presence of purified fibrinogen.

Meanwhile, the fibrinogen/polymer agent activates more and more platelets in cascade-like fashion so that the size and strength of the clot is much greater than that of the normal clot. Additionally, the polymer allows extension of time for the hemostatic polymer clot formation and for increase of the strength of the clot. Since the natural coagulation is endogenously regulated and controlled and is a subject to time-related lysis, such regulation mechanisms limit strength of the adhesivity of the normal clot to that formed within 3–5 minutes. After that time the strength of the normal clot cannot be increased. On the other hand, the polymer is not subject to lysis or to the other physiological regulatory mechanisms and can therefore proceed unhindered for more than 30 minutes and up to several hours.

Hemostatic adhesive agents containing fibrinogen/chitosan have many advantages over other currently available fibrin glues. They provide rapid hemostasis, adhere and glue the damaged tissues together with great strength, and seal ruptures, leaks or punctures of the tissues. The presence of chitosan in the hemostatic agent allows sizable increase in the speed with which the clot is formed or adhesion is achieved, increasing the clot size and strength in cascade-like manner. The hemostatic adhesive also allows time control with respect to when to stop the clotting and clot formation. Since the autologous hemostatic plasma/polymer agents contain the patient's own viable platelets, they actually promote the healing process. Other advantages of the plasma/polymer were discussed above and are the absence of need for addition of foreign proteins, such as bovine and human fibrinogen, thrombin, or other additives.

Studies at the University of California, Davis have indicate that, for example, in trauma patients, an excess of autologous thrombin may also be detrimental as it may lead to a clot formation and stabilization of the hemostatic process and the regulatory mechanism, depending on the trauma. Such clot formation may be detrimental during trauma.

1. Preparation of the Fibrinogen/Chitosan Hemostatic Agent

The fibrinogen/chitosan polymer agent is prepared from plasma obtained from whole blood either of the patient to be treated (autologous plasma) or from human plasma obtained from blood other than of the patient (non-autologous plasma). In the latter case, care is taken to utilize only healthy and uncontaminated full blood. In case of planned surgery, the patient may provide his own blood before the operation so that the plasma is obtained in advance and fibrinogen and platelets are isolated and preserved.

In case of acute injuries or trauma, the hemostatic adhesive agent of this invention is prepared at the time of operation or treatment. Thus, no blood bank, storage, prior collection of blood or isolation of platelets is necessary. However, the agent may be prepared from blood available from a blood bank, if necessary. Under the most optimal conditions, the current adhesive can be prepared quickly from the patient's own plasma without any risk that the patient may encounter immune reactions or become infected from another individual's blood.

The hemostatic adhesive agent is prepared from whole blood by separating red blood cells from plasma and by further isolating and separating isolated platelets. Typically, whole blood is drawn into a buffered anticoagulant agent, such as sodium citrate, and centrifuged to separate the platelets and plasma from the red blood cells. The plasma is removed and centrifuged for a second time, at high speed, to separate the platelets and the plasma.

The hemostatic fibrinogen/chitosan is preferably prepared from about 100 ml of the patient's own blood. The plasma (40 ml) is separated from the patient's own blood, as described above, and utilized as a source of highly purified fibrinogen. The platelets are also separated and preserved separately. Ammonium sulfate is used for the precipitation, isolation and purification of the fibrinogen.

Briefly, about 10 ml of ammonium sulfate, containing about 65–73, preferably 71 g/100 ml $H_2O$, is added slowly and continuously for about 15–20, preferably 17 minutes, or about 0.50–62 ml, preferably 0.58 ml per minute, to about 40 ml of plasma using very fine capillary tubing and syringe pump, in order to assure that only fibrinogen is precipitated. Most preferred rate of addition of the ammonium sulphate is lower than 0.58 ml/minute. Care is taken that the concentration of ammonium sulfate never exceeds 25% saturation in any portion of the plasma. Monitoring of the fibrinogen precipitation from the plasma is best at the tip of the needle or catherer where long stringy threads form. When these threads are translucent and fibrous, there is no precipitation of other proteins. When there are visible granular-like structures, other proteins, such as the euglobulins (IgG, IgM, IgE,), pseudoglobulins, and albumin are precipitating. That happens when the rate and concentration of the ammonium sulphate exceeds 25%. If the fibrinogen is contaminated with these other proteins, the adhesive strength of the hemostatic agent is diminished.

The process for production of isolated and purified fibrinogen by treatment of plasma with addition of small increments of ammonium sulphate is new. In this process, an initial solution of ammonium sulphate in concentration preferably about 71 g/100 ml of water is prepared. About 10 ml of this solution is used for precipitation of fibrinogen from 40 ml of plasma by adding this solution continually for about 17 minutes to 40 ml of plasma in such a way that preferably about 0.58 ml containing about 0.38 g of ammonium sulphate is added to 40 ml plasma volume in one minute. This process assures that only fibrinogen and no other plasma proteins are precipitated. This slow precipitation of fibrinogen constitutes a difference and improvement against previously known methods.

All previously published methods of fibrinogen precipitation have utilized saturated ammonium sulphate solution added to the plasma at the same time which resulted in precipitation of all plasma proteins because the concentration of the ammonium sulfate in the plasma exceeded 25%. Fibrinogen produced by these methods was contaminated with euglobulins and albumin, yielding fibrinogen of inferior adhesive strength. This was evidenced by the presence of an insoluble precipitate fraction present when the fibrinogen obtained by such methods was dissolved in the plasma or an aqueous solvent or medium.

The fibrinogen produced by the novel process for isolation of fibrinogen from other plasma proteins, produces the only precipitate which is fully soluble in plasma or other aqueous media. There are no insoluble precipitates present in the fibrinogen purified and isolated according to the new process. The isolated and purified fibrinogen thus obtained possesses a superior adhesive strength.

The current invention utilizes this superior isolated purified fibrinogen in combination with polymers, preferably chitosan. Chitosan may be added to the purified fibrinogen before or after it is added to the tissue. The admixture of fibrinogen and chitosan may be added to the site of bleeding; the chitosan may be applied directly to the injured tissue followed by fibrinogen; or fibrinogen may be added first, followed by chitosan. The purified fibrinogen and polymer agent traps platelets to activate the conversion of prothrombin to thrombin in the presence of endogenous Ca++, and the platelets undergo disruption and release thromboxans and ADP as already described. This release induces additional platelets to adhere with the clotting factors Va, Xa, Ca++ and prothrombin to the polymer and platelet plasma membranes.

In developing this invention, hemostatic fibrinogen/chitosan was prepared from a pig's blood. The pig's plasma was separated from the blood by centrifugation and utilized as a source of highly purified fibrinogen using ammonium sulphate precipitation according to the invention. The hemostatic agent was then tested for its hemostatic properties on the same pig.

Hemostatic properties of the fibrinogen/chitosan hemostatic agents were additionally prepared and tested on human, pig and rat splenic incisions; arterial incisions; liver wounds, cuts and lacerations; splenic ruptures; and sealing of leaks and fistulas. The hemostatic agents of this invention are thus useful for stopping bleeding from tissue and internal organs, from ruptured vessels, for sealing of common bile duct, and for control of pulmonary leaks and other similar injuries.

2. Polymer Component of the Hemostatic Adhesive

The polymer added to the isolated purified fibrinogen is a highly positively charged polymer, preferably a chitosan, such as chitosan-anionic or more preferably chitosan-cationic, which forms strong and clear bonds and gels when brought in contact with endogenous calcium ions. The chitosan polymers are biodegradable and non-toxic. Chitosan is added in concentration from about 0.1% to about 10%. Addition of chitosan accelerates wound healing and having by itself certain bioadhesive properties, increases adhesivity of the fibrinogen/chitosan hemostatic adhesive agent and also increases adhesivity of separated tissues in gluing them together.

The polymer is dissolved in a small volume, about 0.5–1 ml, of citrate autologous plasma and then added to the fibrinogen.

3. Preparation of the Hemostatic Adhesive Agent

The hemostatic adhesive agent of the invention is prepared by mixing together fibrinogen and the chitosan polymer forming the fibrinogen/chitosan hemostatic agent.

Platelets, preferably autologous, isolated from the same volume of plasma from which the fibrinogen is isolated and purified, are added to the fibrinogen and polymer agent.

The mixture of the fibrinogen/chitosan forms the basic hemostatic adhesive agent of the invention. For the best and fastest hemostasis, exogenous, but preferably autologous, platelets are added either to the basic hemostatic agent or to the site of injury at the same time as the agent is added. The agent may additionally contain other therapeutically active pharmaceutically acceptable agents or pharmaceutically acceptable additives such as a calcium solution, thrombin, antibiotics or enzymes. However, these agents are not necessary as the agent achieves hemostasis solely with the combination of fibrinogen and chitosan.

The agent of the invention is able to stop extensive and large area bleeding from a surface wound, or from the surface of a deep tissue wound, or from an arterial or venous rupture, without addition of exogenous thrombin or any other agent.

In practice, the hemostatic agent is applied over the wound, incision, cut, bleeding surface or other injury. In these cases, the polymer which activates and aggregates the exogenous platelets over the site of injury forms the initial clot and enhances the coagulation activity of the platelets and their normal hemostatic properties and forms a binding surface for endogenous platelets present in the subject's blood. The presence of exogenous and endogenous platelets and high concentrations of readily available plasma proteins in the circulating blood at the bleeding site needed for coagulation allows fast hemostatic action and clotting build-up on and over the initial hemostatic polymer clot.

While it is preferred that the autologous platelet-fibrinogen is used whenever possible, the non-autologous platelets or fibrinogen from other humans is equally useful in cases of emergency and profuse bleeding, when it is impossible or dangerous to obtain autologous blood, and is prepared by the same process and under the same conditions.

When the adhesive agent is prepared in advance, essentially the same procedure is followed except that the fibrinogen and platelets are stored separately in the refrigerator, if the adhesive will be used within 24 hours, or frozen, if the adhesive will be used later. The polymer is stored and preweighed in the desired amount, preferably in an amount which would provide 0.1%–10% dilution with fibrinogen. The volume of the adhesive depends on the extent of the surgery. Typically, both the platelets and fibrinogen are obtained from 40 ml blood, which provides about 1.5–2.5 ml of fibrinogen. To this amount about 0.015 to about 0.25 g of chitosan is added to form the hemostatic adhesive agent. If the wound is over a large area which needs to be sealed, appropriately larger volumes of the agent are prepared.

It is another advantage of the invention that the treating surgeon or physician can determine what volume is necessary to achieve complete adhesion and hemostasis. Also, should the bleeding not be contained by the available volume of the agent, additional volume can be quickly and conveniently prepared.

The addition of the polymer to fibrinogen is responsible for the hemostatic agent's increased adhesivity and strength.

The time for which the hemostatic adhesive is applied controls the extent of the hemostasis and the strength of the adhesion. As a result, the hemostatic agent of the invention is useful for sealing and adhesion of deep tissue wounds, ruptures, or incisions, tears or cuts on the veins. The process for preparation of the hemostatic adhesive agent is fast—typically the hemostatic polymer adhesive can be produced within 3–10 minutes and does not require any special equipment, agents or procedures other than those used in a biochemical medical laboratory on a daily basis.

In cases of autologous platelet-rich plasma, additional advantages are the reduced risk of disease transmission as both the platelets and plasma are obtained from the patient. The immunogenic reactions to the exogenous sources of the thrombin or fibrinogen, typically bovine thrombin or fibrinogen, are eliminated. Presence of living, autologous platelets additionally promotes and expedites healing of tissues.

UTILITY

The hemostatic adhesive agent of the invention is used for treatment of any trauma of the liver, spleen, pancreas, lung, bone, etc., or for cardiovascular and vascular situations, such as microvascular, anastomoses, vascular grafts, intraoperative bleeding and aortic bleeding and repair, for thoracic surgery such as lung biopsy, for transplant of the heart, renal, pancreas, lung, bone or bone marrow, for neurosurgery such as nerve anastomosis, or CSF leak repair, for endoscopic surgery, such as in hepatic trauma, or bile duct repair, for interventional radiology, such as for percutaneous liver biopsy or vascular occlusion, for gastrointestinal surgery such as colonic anastomoses, for obstetrics and gynecology such as rectovaginal fistulas, for pediatric and fetal surgery, for plastic surgery and burn repairs such as grafting process of cultured epidermis, for dermatology such as hair transplants, for dental surgery, for ophthalmic cataract surgery, for urology, for correction of urinary fistulas and such others.

The treatment may be used alone or in combination with other techniques, agents and drugs typically used to correct these problems.

A major difference between this hemostatic adhesive agent preparation and previous fibrin glues is the agent's composition consisting of: the isolated fibrinogen purified of plasma proteins; the polymer; and the autologous living and metabolizing platelets. Purified fibrinogen is able to promote platelet activation leading to a greater conversion of prothrombin to thrombin endogenously, thus eliminating a need for addition of exogenous thrombin. The polymer of the hemostatic agent together with exposed collagen at a site of injury act as a binding site for platelets. The platelets then release other coagulating factors and cofactors, acting in their natural way in promoting coagulation, and assisting also in adhesion of damaged and separated tissues together.

Additionally, the hemostatic adhesive agents of the invention promote and accelerate wound healing because they are made of the patient's own blood components.

The hemostatic fibrinogen/chitosan agent is fully effective as a hemostatic agent without bovine thrombin. The hemostatic agent provides instant hemostasis and adheres damaged tissues together. The healing process is promoted, because fibrinogen/chitosan is combined with the patient's own viable thrombocytes.

The following examples are intended to illustrate the invention and its utility. These examples are not to be interpreted as limiting the invention in any way.

EXAMPLE 1

Preparation of Purified Isolated Fibrinogen

This example illustrates preparation of purified fibrinogen either in nonconcentrated or concentrated form.

A 80–100 ml blood sample was drawn and placed into 0.1055M buffered sodium citrate solution. The tubes were centrifuged at 770×g for 10 minutes and a 40 ml platelet-rich plasma sample was removed. The plasma was centrifuged a second time at 2000×g. Then, the plasma was removed and the platelets were saved. The plasma was purified using ammonium sulphate.

Ammonium sulfate solution was used for precipitation, isolation and purification of the fibrinogen. 10 ml of ammonium sulfate (71 gms/100 ml $H_2O$, 25° C.) was added slowly in increments of 0.58 ml/minute to 40 ml plasma using very fine capillary tubing (PE Intramedic Clay Adams 1. D. 0.015"×0. D. 0.043") and a syringe pump, (Harvard Apparatus I.V. Syringe Pump Model 903). The plasma was spun using magnetic bar 40–60 rpm and mixed as a very fine jet of ammonium sulfate solution was slowly added to 1 cm under the plasma surface. The concentration of the ammonium sulfate was constantly monitored by visual observation of the fibrinogen fiber thread formation and was never allowed to exceed 25% saturation in any portion of the plasma in order that only pure fibrinogen was precipitated. Such monitoring involved control of the speed of the syringe pump combined with observation of the tip of the catherer or needle ejecting the ammonium sulphate. Upon slow ejection of the ammonium sulphate ($\leq 0.58$ ml/minute), formation of the fibrinogen precipitate as threads was observed. The yield of precipitated fibrinogen was 1–2 g/40 ml of nonconcentrated plasma. Concentrated plasma yielded proportionally larger amount of fibrinogen depending on the concentration factor, as described below. Fibrinogen was dissolved in autologous citrate plasma (1 ml at 37° C.) and mixed gently to dissolve the fibrinogen. When the fibrinogen was isolated and purified from the other plasma proteins by the above procedure, the fibrinogen was dissolved without any residue.

When the rate and concentration of the precipitate ammonium sulfate solution addition exceeded 25%, euglobulins, pseudoglobins, and albumin precipitated. This precipitation was evidenced by the presence of proteins which were insoluble when fibrinogen was dissolved in the plasma. When the fibrinogen adhesive was contaminated with other proteins (euglobulins, pseudoglobins, and albumin), the adhesive strength was diminished and hemostatic action was slower. Contaminating albumin and other proteins were found to interfere with fibrin gelation by increasing fibrin solubility. The plasma was either processed as is or it was concentrated by centrifugation through a 30,000 MW cut-off filter, obtained from CentriCell Polysciences, Inc., for 20 minutes. The plasma was concentrated by a factor of 7–8, that is 270–390 mg of fibrinogen present in 100 ml of plasma was concentrated to levels larger than 2000 mg of fibrinogen per 100 ml of plasma.

EXAMPLE 2

Autologous Hemostatic Fibrinogen/Chitosan Agent

This example describes preparation of the hemostatic fibrinogen/chitosan agent from autologous pig's blood for hemostasis of the pig's bleeding spleen.

Hemostatic fibrinogen/chitosan was prepared from 40 ml of a pig's own blood according to Example 1. Plasma was separated from the blood by centrifugation and utilized as a source of fibrinogen. Ammonium sulfate was used for the precipitation of fibrinogen. 10 ml ammonium sulfate (71 gms/100 ml $H_2O$) was added continuously (10 ml/17 minutes or 0.58 ml/minute) to 40 ml plasma using very fine capillary tubing and syringe pump, in order that only fibrinogen was precipitated. The concentration of the ammonium sulfate never exceeded 25% saturation in any portion of the plasma. The precipitated fibrinogen (2.1 ml) was tested for presence of other plasma proteins by dissolving it in 1 ml of pig plasma. The fibrinogen dissolved without any residue confirming absence of any contamination with other plasma proteins. This solution was mixed with 0.2 g of chitosan dissolved in 0.5 ml of the pig's plasma. Resulting hemostatic agent was used to test its hemostatic activity in splenic incision described in Example 4.

EXAMPLE 3

Hemostatic Effect of Fibrinogen/Chitosan Hemostatic Agent

This example illustrates the effect of the fibrinogen/chitosan hemostatic agent administered separately on pig's surgical incision of the spleen.

The pig's abdomen was surgically opened and the spleen was exposed. A surgical incision 3 cm long and 1 cm deep was made in the spleen. The incision bled profusely. Bleeding was controlled by compression and 0.25 g chitosan obtained from Sigma was placed into the spleen incision. The dissolved isolated, purified fibrinogen (1 ml) was combined with the platelets (0.2 ml) obtained from the 40 ml of starting whole blood. The plasma/platelet mixture was added over the chitosan in the spleen incision. The compression was continued for 5 minutes until hemostasis was attained.

Bleeding wounds in humans and other mammals are treated in the same manner. The autologous hemostatic surgical adhesive is obtained from the individual to be treated with such autologous surgical agent.

EXAMPLE 4

Hemostatic Effect of Fibrinogen/Chitosan Hemostatic Agent

This example illustrates the effect of the fibrinogen/chitosan hemostatic agent on a surgical incision of the spleen.

The pig's abdomen was surgically opened and the spleen was exposed. A surgical incision 3 cm long and 1 cm deep was made in the spleen. The incision bled profusely. Bleeding was controlled by a mechanical compression. Hemostatic agent prepared according to Examples 1 and 2, containing 0.25 g chitosan was combined with purified fibrinogen and platelets (0.2 ml) obtained from 40 ml of starting whole blood were added to the site of the bleeding. The mechanical compression was continued for 5 minutes and then the compression was removed. There was still slight bleeding which subsided in another 2–3 minutes. The wound did not reopen and complete hemostasis was thus attained.

Bleeding wounds in humans and other mammals are treated in the same manner. The autologous hemostatic surgical adhesive is obtained from the individual to be treated with such autologous surgical agent.

EXAMPLE 5

Hemostatic Properties of Fibrinogen/Chitosan Hemostatic Agent on Tissue Injury

This example illustrates the adhesive effect of the fibrinogen/chitosan-containing hemostatic adhesive agents on experimentally induced liver trauma and incisions in rats.

The hemostatic agent is prepared as described in Examples 1 and 2 from the rat's blood.

A 250 g rat is anesthetized. A midline incision is made and the surface of the liver is exposed. One lobe of the liver is excised and removed and 1 cm cut is made in another lobe of the liver. The bleeding surfaces of the wounds are sponged dry and the hemostatic agent containing concentrated isolated purified fibrinogen, chitosan and platelets is applied by spray. The fibrinogen/chitosan/platelet adhesive forms a fibrinogen/chitosan clot on contact with the bleeding liver surface and fast hemostatic process begins. A complete hemostasis is attained within 2 minutes.

EXAMPLE 6

Hemostatic Properties of the Fibrinogen/Chitosan Containing Hemostatic Agent on Arterial Incision This example illustrates the adhesive effect of the fibrinogen/chitosan containing hemostatic adhesive agent on an arterial incision.

The hemostatic agent is obtained from 30 ml of rat blood as described in Examples 1 and 2.

A 250 g rat is anesthetized. An incision is made over the femoral artery. The femoral artery is exposed and cleared. The blood flow through the artery is stopped by pressure on the proximal portion of the artery. The artery is cut and divided cleanly horizontally with a scalpel blade and excess blood is sponged dry. The divided artery is held together with forceps and the hemostatic agent is applied. The pressure on the proximal artery is maintained for 2–5 minutes. The hemostatic agents form a clot along the cut surface of the artery and bleeding decreases until it stops. After the compression of the blood flow is relieved, hemostasis is completely maintained with 4–5 minutes. The incision does not reopen.

EXAMPLE 7

Laparoscopically Applied Fibrinogen/Chitosan Adhesive Agent in Liver Trauma

This example illustrates the use of isolated purified fibrinogen/chitosan-containing hemostatic adhesive on liver trauma in domestic swine.

Three domestic swine are anesthetized using intravenous (IV) thiamylal sodium (16.0 mg/kg) and inhaled halothane. Laparoscope is introduced into the peritoneal cavity under sterile conditions. Heparin is administered to create maximal bleeding from the liver laceration. Laceration in the liver lobe about 3 cm long and 2 cm deep is made to induce bleeding from this injury.

About 3 ml of fibrinogen/chitosan/exogenous autologous platelets are administered through the laparoscope to the site of the liver laceration. The extent of bleeding is followed. Bleeding ceases very quickly, typically in 1–4 minutes, in every case.

EXAMPLE 8

Hemostatic Effect of the Adhesive Agent on Liver Injury in Humans

This example illustrates the adhesive effect of the autologous hemostatic agent prepared from the fibrinogen obtained from plasma of the patient's own blood in combination with chitosan.

Patient suffers from ruptured liver. Blood is drawn and autologous concentrated fibrinogen is prepared as described in Example 1. The fibrinogen obtained from about 100 ml of the whole blood is mixed with about 0.3 g chitosan. Upon laparoscopy, the bleeding liver wound is covered with the adhesive fibrinogen/chitosan agent and platelets obtained from the whole blood are applied over the bleeding rupture to stop bleeding. Bleeding is stopped within several minutes. The patient is monitored for internal bleeding but such bleeding does not occur.

EXAMPLE 9

Hemostatic Effect of Combination of Fibrinogen with Chitosan In Situ

This example illustrates the hemostatic effect of combination of isolated purified fibrinogen with chitosan in situ in a human following the bleeding from a ruptured spleen.

Patient suffers from ruptured spleen. Venous blood is drawn and autologous fibrinogen and platelets are prepared from plasma according to Example 1, and separated. The purity of isolated fibrinogen is determined by dissolving the fibrinogen precipitate in 4 ml of plasma. Chitosan (0.3 g) is dissolved in 1 ml of plasma. Peritoneal cavity is opened, the bleeding is temporarily stopped by compression, the chitosan plasma solution is applied over the bleeding surface of the spleen followed by spraying of the fibrinogen plasma solution. Autologous platelets are added in situ to stop the bleeding. Bleeding slows down and stops in about 25–30 minutes.

EXAMPLE 10

Fibrinogen/Chitosan Containing Agent for Sealing of the Common Bile Duct

This example illustrates the sealing ability of the fibrinogen/chitosan-containing adhesive of the invention during and post biliary tract surgery in higher mammals.

Dogs are subjected to the common bile duct surgery. Fibrinogen (2.5 ml) is prepared from their blood according to Examples 1 and 2, and mixed with 0.03 g chitosan, as described. Chitosan is applied over the surgery incision while both sides of the suture are held together. Fibrinogen is added immediately followed by addition of platelets. Platelets are applied to the place of the incision, bleeding and leaking of the bile. Sealing of the bile duct as well as cessation of bleeding is achieved within 8 minutes.

EXAMPLE 11

Use of the Autologous Fibrinogen/Chitosan Agent to Control Pulmonary Leak

This example illustrates the use of the fibrinogen/chitosan adhesive as the measure for control of lung air leaks.

Patient has an obstructive disease due to a lung tumor. After the tumor is removed, the patient has an air leak. The site of the air leak is identified by using bronchoscope. Patient's blood is used to prepare the fibrinogen and chitosan containing adhesive agent according to Examples 1 and 2. For this particular problem, fibrinogen and chitosan (0.15 g/ml) are prepared in more dilute solution 1 ml of fibrinogen and 0.15 g of chitosan are dissolved in 5 ml of plasma. A catheter is placed as close as possible to the site of the leak and the solution is injected through the catheter. Adhesive properties of chitosan in combination with fibrinogen are able to seal the leak without forming an extensive coagulation plug.

The air leak is blocked and sealed by the adhesive within 5–10 minutes. After that time no air leak is detected.

What is claimed is:

1. An improved hemostatic adhesive agent consisting essentially of a mixture of fibrinogen isolated from plasma and purified of other plasma proteins and a biocompatible chitosan polymer, wherein a ratio of the chitosan polymer to the isolated and purified fibrinogen is from about 0.1:10% to about 90:99.9%, w/w, and wherein said fibrinogen is separated from other plasma proteins by precipitation with ammonium sulfate solution having concentration of about 65–73 g per 100 ml, said precipitation comprising the addition of about 10 ml of said ammonium sulfate solution to about 40 ml of plasma continuously in increments from about 0.50 to about 0.62 ml per minute for about 15–20 minutes.

2. A method for attaining hemostasis by administering to a site of injury a hemostatic agent consisting essentially of a mixture of fibrinogen isolated from plasma and purified of other plasma proteins and a biocompatible chitosan polymer, wherein a ratio of the chitosan polymer to the isolated and purified fibrinogen is from about 0.1:10% to about 90:99.9%, w/w, and wherein said fibrinogen is separated from other plasma proteins by precipitation with ammonium sulfate solution having concentration of about 65–73 g per 100 ml, said precipitation comprising the addition of about 10 ml of said ammonium sulfate solution to about 40 ml of plasma continuously in increments from about 0.5 to about 0.62 ml per minute for about 15–20 minutes.

3. The agent of claim 1 wherein the chitosan polymer is anionic or cationic.

4. The agent of claim 3 wherein ammonium sulphate solution is added in increments of no more than about 0.58 ml per minute for about 15–20 minutes.

5. The agent of claim 3 wherein ammonium sulphate solution is added in increments lower than 0.58 ml per minute for about 17 minutes.

6. The agent of claim 5 wherein the concentration of ammonium sulphate in the plasma during precipitation of fibrinogen does not at any time exceed 25%.

7. The agent of claim 6 wherein a ratio of chitosan to fibrinogen is from about 10% to about 90, w/w.

8. The agent of claim 7 wherein the fibrinogen is isolated from plasma obtained from the whole autologous blood.

9. The agent of claim 8 additionally containing platelets separated from autologous plasma said platelets added to said agent at a site of bleeding.

10. The agent of claim 8 administered to a site of bleeding.

11. The agent of claim 10 administered to the site of bleeding as an admixture of chitosan and fibrinogen.

12. The agent of claim 3 wherein the polymer is chitosan cationic.

13. The agent of claim 12 wherein the chitosan polymer is added in the amount from about 1% to about 10%.

14. The method of claim 2 wherein the fibrinogen is autologous.

15. The method of claim 14 wherein autologous platelets are additionally added to the hemostatic.

* * * * *